US007884181B2

(12) United States Patent
Lybeck (Berglund) et al.

(10) Patent No.: US 7,884,181 B2
(45) Date of Patent: Feb. 8, 2011

(54) PHARMACEUTICAL FORMULATION COMPRISING CRYSTALLINE INSULIN AND DISSOLVED INSULIN

(75) Inventors: Petter Lybeck (Berglund), Lund (SE); Charlotte Hammelev, Farum (DK); Lone Eskildsen, Slangerup (DK); Johanne Madsen, Lyngby (DK); Helle Aalund Olsen, Måløv (DK); Lone Kimer, Farum (DK)

(73) Assignee: Novo Nordisk A/S, Bagsvaerd (DK)

( * ) Notice: Subject to any disclaimer, the term of this patent is extended or adjusted under 35 U.S.C. 154(b) by 639 days.

(21) Appl. No.: 11/664,407

(22) PCT Filed: Oct. 5, 2005

(86) PCT No.: PCT/EP2005/055017

§ 371 (c)(1),
(2), (4) Date: Oct. 31, 2007

(87) PCT Pub. No.: WO2006/037784

PCT Pub. Date: Apr. 13, 2006

(65) Prior Publication Data

US 2008/0171694 A1    Jul. 17, 2008

Related U.S. Application Data

(60) Provisional application No. 60/620,143, filed on Oct. 19, 2004.

(30) Foreign Application Priority Data

Oct. 5, 2004    (DK) ............................... 2004 01519

(51) Int. Cl.
*A61K 38/00*    (2006.01)
(52) U.S. Cl. ..................................... 530/304; 530/305
(58) Field of Classification Search .................... None
See application file for complete search history.

(56) References Cited

U.S. PATENT DOCUMENTS

| 5,461,031 | A | 10/1995 | DeFelippis |
| 5,474,978 | A | 12/1995 | Bakaysa et al. |
| 5,547,930 | A | 8/1996 | Balschmidt |
| 5,834,422 | A | 11/1998 | Balschmidt |
| 5,866,538 | A | 2/1999 | Norup et al. |
| 5,948,751 | A | 9/1999 | Kimer et al. |
| 6,127,334 | A | 10/2000 | Kimer et al. |

FOREIGN PATENT DOCUMENTS

| CN | 1222084 | 7/1999 |
| EP | 921812 | 11/2001 |
| GB | 889769 | 2/1962 |
| GB | 2290294 | 12/1995 |
| WO | 97/48413 | 12/1997 |
| WO | WO 97/48413 | 12/1997 |

OTHER PUBLICATIONS

Brange, J et al, Chemical Stability of Insulin, Acta. Pharm. Nord., 1992, 149-158, vol. 4—No. 3.
Dodd, S.W. et al, Reversible Adsorption of Soluble Hexameric Insulin onto the Surface of Insulin Crystals Cocrystallized with Protamine: An Electrostatic Interaction, Pharmaceutical Research, 1995, 60-68, vol. 12—No. 1, Plenum Publishing Corporation.

*Primary Examiner*—Suzanne M. Noakes
(74) *Attorney, Agent, or Firm*—Rosemarie R. Wilk-Orescan

(57) ABSTRACT

The invention provides a pharmaceutical formulation and a method for preparing the formulation.

4 Claims, No Drawings

PHARMACEUTICAL FORMULATION COMPRISING CRYSTALLINE INSULIN AND DISSOLVED INSULIN

CROSS-REFERENCE TO RELATED APPLICATIONS

This application is a 35 U.S.C. §371 national stage application of International Patent Application PCT/EP2005/055017 (published as WO 2006/037789), filed Oct. 5, 2005, which claimed priority of Danish Patent Application PA 2004 01519, filed Oct. 5, 2004; this application further claims priority under 35 U.S.C. §119 of U.S. Provisional Application 60/620,143, filed Oct. 19, 2004.

The present invention relates to a pharmaceutical formulation of dissolved insulin, an analogue or derivative thereof and crystalline insulin, or an analogue or derivative thereof. The preparations have superior chemical characteristics.

BACKGROUND OF THE INVENTION

In the treatment of diabetes mellitus, many varieties of insulin preparations have been suggested and used, such as regular insulin, Semilente® insulin, isophane insulin, insulin zinc suspensions, protamine zinc insulin, and Ultralente® insulin. As diabetic patients are treated with insulin for several decades, there is a major need for safe and life quality improving insulin preparations. Some of the commercial available insulin preparations are characterized by a fast onset of action and other preparations have a relatively slow onset but show a more or less prolonged action. Fast acting insulin preparations are usually solutions of insulin, while retarded acting insulin preparations can be suspensions containing insulin in crystalline and/or amorphous form precipitated by addition of zinc salts alone or by addition of protamine or by a combination of both.

In addition, some patients are using preparations having both a fast onset of action and a more prolonged action. Such a preparation may be an insulin solution wherein protamine insulin crystals are suspended. The invention relates to such a suspension in a premixed form.

Acta Pharmaceutica Nordica 4(4), 1992, pp. 149-158 discloses insulin preparations in which the NaCl concentration has been varied in the range of 0 to 250 mM. The major part of the preparations, including all preparations which additionally comprise glycerol, contains a rather high amount of NaCl, i.e. 0.7% corresponding approximately to a concentration of 120 mM. It is stated in this document that whereas NaCl has a stabilizing effect on insulin preparations, glycerol and glucose leads to increased chemical deterioration.

U.S. Pat. No. 5,866,538 discloses insulin preparations with glycerol and/or mannitol and low NaCl concentrations. This reference does not describe suspensions or the presence of protamine.

U.S. Pat. No. 6,127,334 discloses suspensions of insulin AspB28 containing hydrochloric acid, $ZnCl_2$ solution, protamine sulphate solution, m-cresol, phenol, glycerol, disodium monohydrogenphosphate and water. Other examples include the ingredients above including mannitol and/or NaCl and/or LYS$^{B28}$-Pro$^{B29}$-insulin. The examples thus differs in as well ingredients as methods of preparing the formulation. The preparations solve the problem of providing suspensions which are resistant to physical stress.

U.S. Pat. No. 5,547,930 describes solutions of AspB28 insulin containing hydrochloric acid, $ZnCl_2$ solution, protamine sulphate solution, m-cresol, phenol, glycerol, di-sodium monohydrogenphosphate and water. The examples thus differs in as well ingredients as methods of preparing.

The invention thus provides a novel formulation for insulin suspensions, and a novel method of preparing the formulation.

DESCRIPTION OF THE INVENTION

By "insulin analogue" as used herein is meant a polypeptide which has a molecular structure which formally can be derived from the structure of a naturally occurring insulin, for example that of human insulin, by deleting and/or substituting at least one amino acid residue occurring in the natural insulin and/or by adding at least one amino acid residue. The added and/or substituted amino acid residues can either be codable amino acid residues or other naturally occurring amino acid residues or purely synthetic amino acid residues. In an aspect of the invention a maximum of 6 amino acids are amended. In an aspect of the invention a maximum of 5 amino acids are amended. In an aspect of the invention a maximum of 4 amino acids are amended. In an aspect of the invention a maximum of 3 amino acids are amended. In an aspect of the invention a maximum of 2 amino acids are amended. In an aspect of the invention 1 amino acids is amended.

The insulin analogues may be such wherein position 28 of the B chain may be modified from the natural Pro residue to Asp, Lys, or Iie. Also, Asn at position A21 may be modified to Ala, Gln, Glu, Gly, His, Iie, Leu, Met, Ser, Thr, Trp, Tyr or Val, in particular to Gly, Ala, Ser, or Thr and preferably to Gly. Furthermore, Asn at position B3 may be modified to Lys or Asp. Further examples of insulin analogues are des(B30) human insulin, insulin analogues wherein one or both of B1 and B2 have been deleted; insulin analogues wherein the A-chain and/or the B-chain have an N-terminal extension and insulin analogues wherein the A-chain and/or the B-chain have a C-terminal extension. Further insulin analogues are such wherein. One or more of B26-B30 have been deleted. If one or more of the amino acid residues in the positions B26-B30 have been deleted the C-terminal amino acid residue of the B-chain will Lys. In an aspect of the invention the insulin analogue is AspB$^{28}$.

By "insulin derivative" as used herein is meant a naturally occurring insulin or an insulin analogue which has been chemically modified, e.g. by introducing a side chain in one or more positions of the insulin backbone or by oxidizing or reducing groups of the amino acid residues in the insulin or by converting a free carboxylic group to an ester group or to an amide group. Other derivatives are obtained by acylating a free amino group or a hydroxy group.

In the context of the present invention the term "about" means within a reasonable range around the stated value. The term may represent the range which is determined by the accuracy of measurement. In other embodiments the term "about" is within +/−10% of the value.

In the context of the present invention "a" or "an" means one or more.

In the present context the unit "U" approximately corresponds to 6 nmol/mL

In the present invention the amount of a salt refers to the amount of salt added to the insulin preparation, for example in the form of NaCl. In the formulation other sources of salt may exist. However, in the present invention the amount of salt present refers to external addition of salt.

In the present context salt means a physiological acceptable salt. In an aspect of the invention the salt is derived from Lithium, Sodium, Potassium, Magnesium or Calcium, and Cl, Br, $SO_4^{2-}$, $PO_4^{3-}$. In an aspect of the invention the salt is NaCl.

In the present invention "a phenolic compound" refers to phenol itself, derivatives thereof and mixtures of phenol and/or its derivatives. Derivatives of phenol are for example cresol in the different isomers o-, m- and p-cresol. In an aspect of the invention the cresol used in the present invention is m-cresol. In an aspect of the invention a phenolic compound means a mixture of phenol and m-cresol.

The present invention relates to a pharmaceutical formulation comprising crystalline insulin, an analogue or derivative thereof and dissolved insulin, an analogue or derivative thereof, further comprising:

protamine, $Zn^{2+}$, buffer, an isotonic agent, a phenolic compound and salt in the amount of above 3 mM. In an aspect of the invention the amount of added salt is below 50 mM. In an aspect of the invention salt is added in an amount of 7 to 40 mM. In an aspect of the invention salt is added in an amount of 10-30 mM in the final preparation. In an aspect of the invention salt is added in an amount of 13-26 mM of final preparation. In an aspect of the invention salt is added in the amount of 17-23 mM in the final preparation. In an aspect of the invention salt is added in the amount of 10 mM of final preparation. In an aspect of the invention salt is added in the amount of 15 mM of final preparation. In an aspect of the invention salt is added in the amount of 20 mM of final preparation.

In a preferred embodiment the pharmaceutical formulation comprises both dissolved insulin, an analogue or derivative thereof, and precipitated, preferably crystalline, insulin or analogues or derivatives thereof in different weight ratios. In an aspect of the invention the pharmaceutical formulation relates to insulin, analogues or derivatives thereof in a weight ratio of dissolved insulin, an analogue or derivative thereof, to crystalline insulin, analogues or derivatives thereof from 1:99 to 99:1; In an aspect of the invention the preparations comprise a weight ratio of dissolved insulin, an analogue or derivative thereof, to crystalline insulin, analogues or derivatives thereof, of 5:95, 10:90, 15:85, 20:80, 25:75, 30:70, 35:65, 40:60, 45:55, 50:50, 55:45, 60:40, 65:35, 70:30, 75:25, 80:20, 85:15, 90:10, and 95:5—and includes the intervals between the specifically mentioned relations. In an aspect of the invention the preparation relates to insulin $AspB^{28}$ in a suspension comprising a weight ratio of dissolved to crystalline insulin $AspB^{28}$ of 30:70. In an aspect of the invention the preparation relates to insulin $AspB^{28}$ in a suspension comprising a weight ratio of dissolved to crystalline insulin $AspB^{28}$ of 70:30. In an aspect of the invention the preparation relates to insulin $AspB^{28}$ in a suspension comprising a weight ratio of dissolved to crystalline insulin $AspB^{28}$ of 80:20. In an aspect of the invention the preparation relates to insulin $AspB^{28}$ in a suspension comprising a weight ratio of dissolved to crystalline insulin $AspB^{28}$ of 20:80. In an aspect of the invention the preparation relates to insulin $AspB^{28}$ in a suspension comprising a weight ratio of dissolved to crystalline insulin $AspB^{28}$ of 50:50.

In an aspect of the invention the preparations contains between 600 and 6000 nmol/mL of insulin, an analogue or derivative thereof. In an aspect of the invention the preparations contain 100 U/mL of insulin, an analogue or derivative thereof. In an aspect of the invention the preparations contain 200 U/mL of insulin, an analogue or derivative thereof.

The amount of protamine determines the amount of crystalline insulin, an analogue or derivative thereof, in the formulation. The amount of protamine determines the weight ratio of dissolved insulin, an analogue or derivative thereof to crystalline insulin, an analogue or derivative thereof and is adjusted accordingly. In an embodiment of the invention protamine used is between 0.01 to 5.0 mg/ml.

In an aspect of the invention Zinc is added. Zinc may wholly or partially originate from a Zinc salt such as Zinc chloride, Zinc sulphate or Zinc acetate. In an aspect of the invention the Zinc added is in the form of Zinc chloride. The amount of $Zn^{2+}$ added is from 2 $Zn^{2+}$:6 insulin to 5 Zn:6 insulin.

In an aspect of the invention the formulation comprises an isotonic agent. In an aspect of the invention the isotonic agent is selected from the group consisting of a sugar or sugar alcohol, an amino acid (e.g. L-glycine, L-histidine, arginine, lysine, isoleucine, aspartic acid, tryptophan, threonine), an alditol (e.g. glycerol (glycerine), 1,2-propanediol (propyleneglycol), 1,3-propanediol, 1,3-butanediol) polyethyleneglycol (e.g. PEG400), or mixtures thereof. Any sugar such as mono-, di-, or polysaccharides, or water-soluble glucans, including for example fructose, glucose, mannose, sorbose, xylose, maltose, lactose, sucrose, trehalose, dextran, pullulan, dextrin, cyclodextrin, soluble starch, hydroxyethyl starch and carboxymethylcellulose-Na may be used. In one embodiment the sugar additive is sucrose. Sugar alcohol is defined as a C4-C8 hydrocarbon having at least one —OH group and includes, for example, mannitol, sorbitol, inositol, galactitol, dulcitol, xylitol, and arabitol. In one embodiment the sugar alcohol additive is mannitol. The sugars or sugar alcohols mentioned above may be used individually or in combination. There is no fixed limit to the amount used, as long as the sugar or sugar alcohol is soluble in the liquid preparation and does not adversely effect the stabilizing effects achieved using the methods of the invention. In an aspect of the invention the isotonicity agent included in the preparations is glycerol.

A pharmaceutical formulation according to any of the above embodiments wherein the isotonicity agent is present in the amount of 130-225 mM of final preparation. In an aspect of the invention the isotonicity agent is present in the amount of 150-200 mM of final preparation. In an aspect of the invention the isotonicity agent is present in the amount of 160-190 mM of final preparation. In an aspect of the invention the isotonicity agent is present in the amount of 170-180 mM of final preparation. In an aspect of the invention the isotonicity agent is present in an amount of about 174 mM of final preparation. In an aspect of the above the isotonicity agent is glycerol.

In an aspect of the invention buffers are included in the preparations. Suitable buffers are in principle any pharmaceutically acceptable buffer for human administration. In a further embodiment of the invention the buffer is selected from the group consisting of sodium acetate, sodium carbonate, citrate, glycylglycine, histidine, glycine, lysine, arginine, sodium dihydrogen phosphate, disodium hydrogen phosphate, sodium phosphate, and tris(hydroxymethyl)-aminomethan, bicine, tricine, malic acid, succinate, maleic acid, fumaric acid, tartaric acid, aspartic acid or mixtures thereof. Each one of these specific buffers constitutes an alternative embodiment of the invention. In an aspect of the invention the buffer is a sodiumphosphate buffer. In an aspect of the invention the buffer is disodiumphosphate dihydrate.

In an aspect of the invention buffer is in the amount of 2-20 mM. In an aspect of the invention buffer is in the amount of 6-10 mM. In an aspect of the invention the amount of buffer is 7 mM. In an aspect of the invention the buffer is a sodiumphosphate buffer. In an aspect of the invention the buffer is disodiumphosphate dihydrate.

The invention provides a method for the preparation of a pharmaceutical composition according to the present invention comprises the steps of
a) providing an acidic solution comprising insulin, an analogue og derivative thereof, a source of zinc, a suitable amount of protamine, optionally further comprising phenolic compound, and/or an isotonicity agent, and/or salt and
b) providing an alkaline solution comprising a substance which acts as a buffer at physiological pH, and optionally further comprising salt, and/or phenolic compound and/or isotonicity agent, and
c) mixing the acidic and alkaline solutions and
d) leaving the mixture to form the pharmaceutical composition which comprises a soluble phase comprising the dissolved insulin, an analogue or derivative thereof, and a phase with the crystalline insulin, an analogue or derivative thereof, and optionally adjusting pH and optionally adding remaining salt, and/or isotonicity agent and/or a phenolic compound.

In aspects of the above the isotonicity agent is glycerol. In aspects of the above the insulin analogue is $AspB^{28}$.

In an aspect the preparation is performed by mixing a basic solution (Solution I) comprising a buffer, optionally comprising a phenolic compound and/or salt, and/or glycerol with an acidic solution (Solution II) comprising insulin, a source of zinc, a suitable amount of protamine, optionally further comprising salt and/or glycerol, and/or a phenolic compound. The combined solution is then optionally adjusted with regards to volume and pH value and allowed to crystallise. Optionally the remaining of the phenolic compound and/or glycerol and/or salt is then added. The pH value of the final preparation is preferable in the range 7.0 to 7.8.

In an aspect of the invention the combined solution left for crystallisation contains 10 to 1000 U/mL of insulin, an analogue or derivative thereof. In an aspect of the invention the combined solution left for crystallisation contains 100 U/mL of insulin, an analogue or derivative thereof. In an aspect of the invention the combined solution left for crystallisation contains 200 U/mL of insulin, an analogue or derivative thereof. In an aspect of the invention the combined solution left for crystallisation contains 400 U/mL of insulin, an analogue or derivative thereof. In an aspect of the method the insulin analogue is $AspB^{28}$.

In an aspect of the invention salt, isotonicity agent and a phenolic compound are only in solution I. In an aspect of the invention salt, isotonicity agent and a phenolic compound are only in solution II. In an aspect of the invention salt, isotonicity agent and a phenolic compound are divided in both solution I and II.

In an aspect of the invention the combined solution left for crystallisation contains only a fraction of the total amount of isotonicity agent and a phenolic compound, and salt. After crystallisation the remaining amount of a phenolic compound, and/or salt and/or isotonicity agent is added. In an aspect of the invention the combined solution left for crystallisation contains the total amount of salt, only a fraction of the isotonicity agent and only a fraction of the total amount of a phenolic compound. After crystallisation the remaining amount of a phenolic compound and isotonicity agent is added. In an aspect of the invention the combined solution left for crystallisation contains the total amount of a phenolic compound, salt and isotonicity agent.

In an aspect of the invention the total amount of a phenolic compound is divided between the solutions I and II. In an aspect of the invention the amount of a phenolic compound is divided into equal amounts between solution I and II.

In an aspect of the invention 0-100% of the total amount of a phenolic compound is added in the mixture left for crystallisation. In an aspect of the invention 10-90% of the total amount of a phenolic compound is added in the mixture left for crystallisation. In an aspect of the invention 20-85% of the total amount of a phenolic compound is added in the mixture left for crystallisation. In an aspect of the invention 30-80% of the total amount of a phenolic compound is added in the mixture left for crystallisation. In an aspect of the invention 40-75% of the total amount of a phenolic compound is added in the mixture left for crystallisation. In an aspect of the invention 50-70% of the total amount of a phenolic compound is added in the mixture left for crystallisation. In an aspect of the invention 55-65% of the total amount of a phenolic compound is added in the mixture left for crystallisation. In an aspect of the invention 60% of the total amount of a phenolic compound is added in the mixture left for crystallisation. In an aspect of the invention 80% of the total amount of a phenolic compound is added in the mixture left for crystallisation. In an aspect of the invention 100% of the total amount of a phenolic compound is added in the mixture left for crystallisation. In an aspect of the invention the remaining a phenolic compound is added separately.

In an aspect of the invention the a phenolic compound is a phenolic compound. In an aspect the phenolic compound is phenol or m-cresol, or phenol and m-cresol.

In an aspect of the invention the phenolic compound is present in 20-40 mM of final preparation. In an aspect of the invention phenolic compound is present in 32 mM of final preparation. In an aspect of the invention phenol is present in 10-40 mM of final preparation. In an aspect of the invention phenol is present in 32 mM of final preparation. In an aspect of the invention this phenolic compound comprises phenol in the amount of 10-20 mM of final preparation. In an aspect of the invention the phenolic compound comprises phenol in the amount of 14-18 mM. In an aspect of the invention the phenolic compound comprises phenol in the amount of 16 mM of final preparation.

In an aspect of the invention m-cresol is present in 10-40 mM of final preparation. In an aspect of the invention m-cresol is present in 32 mM of final preparation. In an aspect of the invention the phenolic compound comprises m-cresol in the amount of 10-20 mM. In an aspect of the invention the phenolic compound comprises m- cresol in the amount of 14-18 mM. In an aspect of the invention the phenolic compound comprises m-cresol in the amount of 16 mM of final preparation. In an aspect of the invention the phenolic compound comprises m-cresol in the amount of 16 mM of final preparation.

In an aspect of the invention both phenol and m-cresol according to the above aspects are present in the final pharmaceutical formulation.

The above insulin preparation has a good ability to resuspend. As the product is a suspension, the end user has to resuspend the product to have a uniform distribution of the product for injection. If the product is not resuspendable the product must be discarded.

This can be controlled by the following procedure: The product is shaken and visually inspected by the human eye at a source of light. The product must be white and homogeneous.

In an aspect of the invention the resuspending of the product comprises a rolling of the product followed by upside-down turning of the product.

The present invention is particularly advantageous in connection with suspensions comprising analogues of human insulin.

The invention is further illustrated by the following examples which, however, are not to be construed as limiting.

EXAMPLE I

An insulin preparation containing both dissolved and crystalline AspB$^{28}$ human insulin was prepared in the following way:

Solution I was prepared, by dissolving 2.50 g disodium phosphate dihydrate and 1.17 g sodium chloride in Water for Injection. 1.55 g phenol, 1.77 g metacresol, 16 g glycerol and 4.32 g sodium hydroxide 2N was added during mixing. The pH of the solution was measured to approx. 9 and water was added to 900 ml. Solution II was prepared by dissolving 1.17 g sodium chloride, 1.77 g metacresol, 1.55 g phenol and 16 g glycerol in water. Then 0.45 g protamine sulphate in solution was added to the solution while mixing and 7.5 g of AspB$^{28}$ human insulin dissolved in water by adding to it 3.4 g 2 N hydrochloric acid and 1.04 g zinc chloride solution (4 mg/ml), was added to the solution while mixing. Water ad 800 ml was added. The solutions were mixed and the pH of the suspension was, if necessary, read-justed to approx. 7.2 by adding sodium hydroxide or hydrochloric acid. Water ad 2000 ml was added.

The resulting suspension was now allowed to crystallise. The shape of the crystals and the amount of amorphous particles were checked by microscopy.

In the resulting preparation, the weight ratio of precipitated to dissolved insulin was 50:50.

EXAMPLE II

An insulin preparation containing both dissolved and crystalline AspB$^{28}$ human insulin was prepared in the following way:

Solution I was prepared, by dissolving 2.50 g disodium phosphate dihydrate and 0.88 g sodium chloride in Water for Injection. 1.24 g phenol, 8 g glycerol and 4.6 g sodium hydroxide 2N was added during mixing. The pH of the solution was measured to approx. 10 and water was added to 450 ml. Solution II was prepared by dissolving 0.88 g sodium chloride, 1.24 g phenol and 4 g glycerol in water. Then 0.64 g protamine sulphate in solution was added to the solution while mixing and 7.5 g of AspB$^{28}$ human insulin dissolved in water by adding to it 3.4 g 2 N hydrochloric acid and 1.04 g zinc chloride solution (4 mg/ml), was added to the solution while mixing. Water ad 500 ml was added. The solutions were mixed and the pH of the suspension was, if necessary, read-justed to approx. 7.2 by adding sodium hydroxide or hydrochloric acid. Water ad 1000 ml was added.

The resulting suspension was now allowed to crystallise. The shape of the crystals and the amount of amorphous particles were checked by microscopy.

Solution III was prepared, by dissolving 0.62 g phenol, 3.54 g of metacresol and 16 g of glycerol. Water was added to 900 ml. Solution III and the crystallization mixture were mixed and the pH of the suspension was, if necessary, read-justed to 7.2 by adding sodium hydroxide or hydrochloric acid. Water ad 2000 ml was added.

In the resulting preparation, the weight ratio of precipitated to dissolved insulin was 70:30.

The invention claimed is:

1. A method for preparing a pharmaceutical product comprising Asp$^{B28}$ human insulin, protamine, Zn$^{++}$, an isotonicity agent, a phenolic compound, and salt in the amount of from about 7mM to about 40mM, wherein the weight ratio of dissolved to crystalline Asp$^{B28}$ human insulin is 30:70, said method comprising the steps of:
   a) providing an acidic solution comprising insulin Asp$^{B28}$ human, a source of zinc, a suitable amount of protamine, optionally further comprising a phenolic compound, and/or an isotonicity agent, and/or salt,
   b) providing an alkaline solution comprising a substance which acts as a buffer at physiological pH, and optionally further comprising salt, and/or a phenolic compound and/or isotonicity agent,
   c) mixing the acidic and alkaline solutions,
   d) leaving the mixture to form the pharmaceutical composition which comprises a soluble phase comprising the dissolved Asp$^{B28}$ human insulin, and a phase with the crystalline Asp$^{B28}$ human insulin, wherein the crystallization mixture contains from about 20% to about 85% of the total amount of phenolic compound in the end product,
   e) adding the remaining phenolic compound and optionally adjusting pH and optionally adding remaining salt, and/or isotonicity agent,
   wherein the phenolic compound is selected from the group consisting of phenol, m-cresol, or a mixture thereof, and wherein m-cresol is only added in step e).

2. The method according to claim 1, wherein the isotonicity agent is glycerol.

3. The method according to claim 1, further comprising the step of adjusting the pH value of the pharmaceutical formulation to a pH of about 7.0-7.8.

4. The method according to claim 1, wherein the formulation is useful for parenteral administration.

* * * * *